US012691240B2

(12) United States Patent (10) Patent No.: US 12,691,240 B2
Veasey et al. (45) Date of Patent: Jul. 28, 2026

(54) TRACHEOSTOMY TUBES AND THE MANUFACTURE OF SUCH TUBES AND THEIR COMPONENTS

(71) Applicant: SMITHS MEDICAL INTERNATIONAL LIMITED, Ashford (GB)

(72) Inventors: Neil Steven Veasey, Ashford (GB); Christopher John Woosnam, London (GB); Laura Beth Morton, Sevenoaks (GB); Ayesha Bint-E-Siddiq, Folkestone (GB); Andrew Thomas Jeffrey, Romney Marsh (GB)

(73) Assignee: ICU MEDICAL INTERNATIONAL LIMITED, Ashford (GB)

( * ) Notice: Subject to any disclaimer, the term of this patent is extended or adjusted under 35 U.S.C. 154(b) by 581 days.

(21) Appl. No.: 18/266,751

(22) PCT Filed: Dec. 19, 2021

(86) PCT No.: PCT/GB2021/000145
§ 371 (c)(1),
(2) Date: Jun. 12, 2023

(87) PCT Pub. No.: WO2022/153019
PCT Pub. Date: Jul. 21, 2022

(65) Prior Publication Data
US 2024/0042151 A1 Feb. 8, 2024

(30) Foreign Application Priority Data
Jan. 14, 2021 (GB) ...................................... 2100454

(51) Int. Cl.
*A61M 16/04* (2006.01)
*A61M 39/02* (2006.01)

(52) U.S. Cl.
CPC .... *A61M 16/0465* (2013.01); *A61M 16/0402* (2014.02); *A61M 16/0497* (2013.01); *A61M 39/0247* (2013.01); *A61M 16/0434* (2013.01); *A61M 2039/0252* (2013.01); *A61M 2039/0261* (2013.01); *A61M 2205/0216* (2013.01); *A61M 2207/00* (2013.01)

(58) Field of Classification Search
CPC ......... A61M 16/04–0497; A61M 16/06–0694; A61M 39/0247; A61M 2039/0252; A61M 2039/0261; A61M 2205/0216; A61M 2207/00
See application file for complete search history.

(56) References Cited

U.S. PATENT DOCUMENTS 5,054,482 A * 10/1991 Bales ................ A61M 16/0497
128/207.14
2009/0288665 A1* 11/2009 Coates .............. A61M 16/0443
128/207.14
2013/0255693 A1* 10/2013 Depel ............... A61M 16/0465
29/428

* cited by examiner

*Primary Examiner* — Valerie L Woodward
(74) *Attorney, Agent, or Firm* — Louis Woo

(57) ABSTRACT

A tracheostomy tube flange (13) of a liquid silicone material has openings (14) towards opposite ends for receiving ends of a neck strap. The openings (14) are reinforced with overmoulded inserts (137, 138) of a heat cured silicone material having a similar hardness to that of the flange material. The inserts (137, 138) have an outwardly-projecting ledge (144) between their ends.

11 Claims, 3 Drawing Sheets

TRACHEOSTOMY TUBES AND THE MANUFACTURE OF SUCH TUBES AND THEIR COMPONENTS

This invention relates to tracheostomy tubes of the kind including a shaft and a mounting flange towards the machine end of the shaft, the mounting flange extending radially outwardly of the tube and being provided with an opening towards each end to which means can be secured to retain the tube with the patient's neck.

Tracheal tubes are used to enable ventilation, respiration or spontaneous breathing of a patient. Endotracheal tubes are inserted via the mouth or nose so that one end locates in the trachea and the other end locates outside the patient. Tracheostomy tubes are inserted into the trachea via a surgically formed opening in the neck. Tracheostomy tubes can be inserted by different techniques, such as the surgical cut-down procedure carried out in an operating theatre or a cricothyroidotomy procedure, which may be carried out in emergency situations.

Tracheostomy tubes are generally used for more long-term ventilation or where it is not possible to insert an airway through the mouth or nose. The patient is often conscious while breathing through a tracheostomy tube, which may be open to atmosphere or connected by tubing to some form of ventilator. The tube is secured in position on the patient's neck by means of a mounting flange fixed with the machine end of the shaft of the tube and positioned to extend outwardly on opposite sides of the tube. A neck tie or the like is passed around the patient's neck and its ends are secured to either end of the flange. Alternatively, sutures can be used to secure the flange in place.

Tracheostomy tubes can be made of various materials and are usually of a bendable plastics material such as PVC, polyurethane or silicone. Silicone is particularly suitable because of the softness, comfort and conformability the material provides. This is a particular advantage in tracheostomy tubes since the patient may be intubated and using a breathing machine for an extended time, usually more than one week. Silicone also has an advantage because it is not damaged by the high temperatures of an autoclave, thereby enabling a silicone tube to be cleaned and autoclaved for reuse.

It is particularly desirable for the mounting flange of a tracheostomy tube to be moulded from a soft, conformable plastics such as silicone so that it flexes readily to conform to the surface of the patient's neck. However, flanges moulded of a soft plastics material it can create problems in that the material may not be strong enough to ensure that the neck strap or sutures do not tear the flange where it is threaded through the openings used to secure the tube to the patient's neck. Mounting flanges made of some silicone materials, such as liquid silicone rubber have a poor abrasion resistance, particularly to abrasion by ties of a relatively stiff material such as those using hook and loop (Velcro) type fasteners. Over several days the abrasion can be so severe that it breaks through the edges of the openings in the flange. This can cause decannulation if not noticed by the care giver. A similar problem can exist where sutures are used with the flange. In an attempt to reduce this risk, it has been proposed to add a reinforcement member of a harder plastics around the neck tie openings, such as described in U.S. Pat. No. 9,457,164. These reinforcement members create a problem of ensuring that the insert does not separate from the remainder of the flange because of the different compositions of the flange and inserts. In general, it is necessary to prime the contact region between the insert and the flange to reduce the risk that the insert does not peel, break free or separate from the flange. Flexing of the flange material relative to the inserts can allow micro fissures and crevices to develop in the flange material that can harbour bacteria leading to infection of the stoma. It is important to ensure that any reinforcement member does not separate from the flange since any such loose member could be inhaled or provide concern that it has been inhaled. Certain materials used to reinforce the flange openings might be damaged by elevated temperatures, thereby making the entire tube unsuitable for autoclave cleaning.

It is an object of the present invention to provide an alternative tracheostomy tube and a method of manufacturing such tubes and their flanges.

According to one aspect of the present invention there is provided a tracheostomy tube of the above-specified kind, characterised in that the flange is of a first silicone material overmoulded on two reinforcement inserts at respective ones of the openings, and that the reinforcement inserts are of a heat-cured silicone rubber material different from the first silicone material.

The silicone material of the flange and of the inserts preferably have a similar hardness. The hardness of both silicone materials is approximately 70 shore A. The first silicone material is preferably a liquid silicone rubber. The inserts may include a hollow tubular body with a passage extending therethrough and a projection extending outwardly of the body between opposite ends. The projection may be an annular ledge extending around the body. Opposite sides of the flange preferably lie level with opposite ends of the body of the inserts, with the passage through each body extending through the thickness of the flange, and with both sides of the projection being covered by material of the flange.

According to another aspect of the present invention there is provide a method of manufacture of a mounting flange of a tracheostomy tube including the steps of moulding two inserts of a heat-cured silicone rubber material, both inserts having a passage therethrough and an outer projection, and overmoulding the two inserts about their outer projection with a silicone material different from that of the inserts to form a mounting flange of the tube where the passage through each insert provides an opening towards opposite ends of the flange to which securing means can be secured.

The silicone material of the inserts preferably has substantially the same hardness as the silicone material overmoulded about the inserts.

According to a further aspect of the present invention there is provided a method of manufacture of a tracheostomy tube including the steps of manufacturing a mounting flange by a method according to the above other aspect of the present invention, providing a shaft of the tube with a patient end and a machine end, and attaching the mounting flange with the shaft towards the machine end of the shaft.

According to a fourth aspect of the present invention there is provided a tracheostomy tube made according to the method of the further aspect of the present invention.

A tracheostomy tube with a mounting flange and a method of manufacture of the mounting flange and tube according to the present invention will now be described, by way of example, with reference to the accompanying drawings in which.

Figure 1:
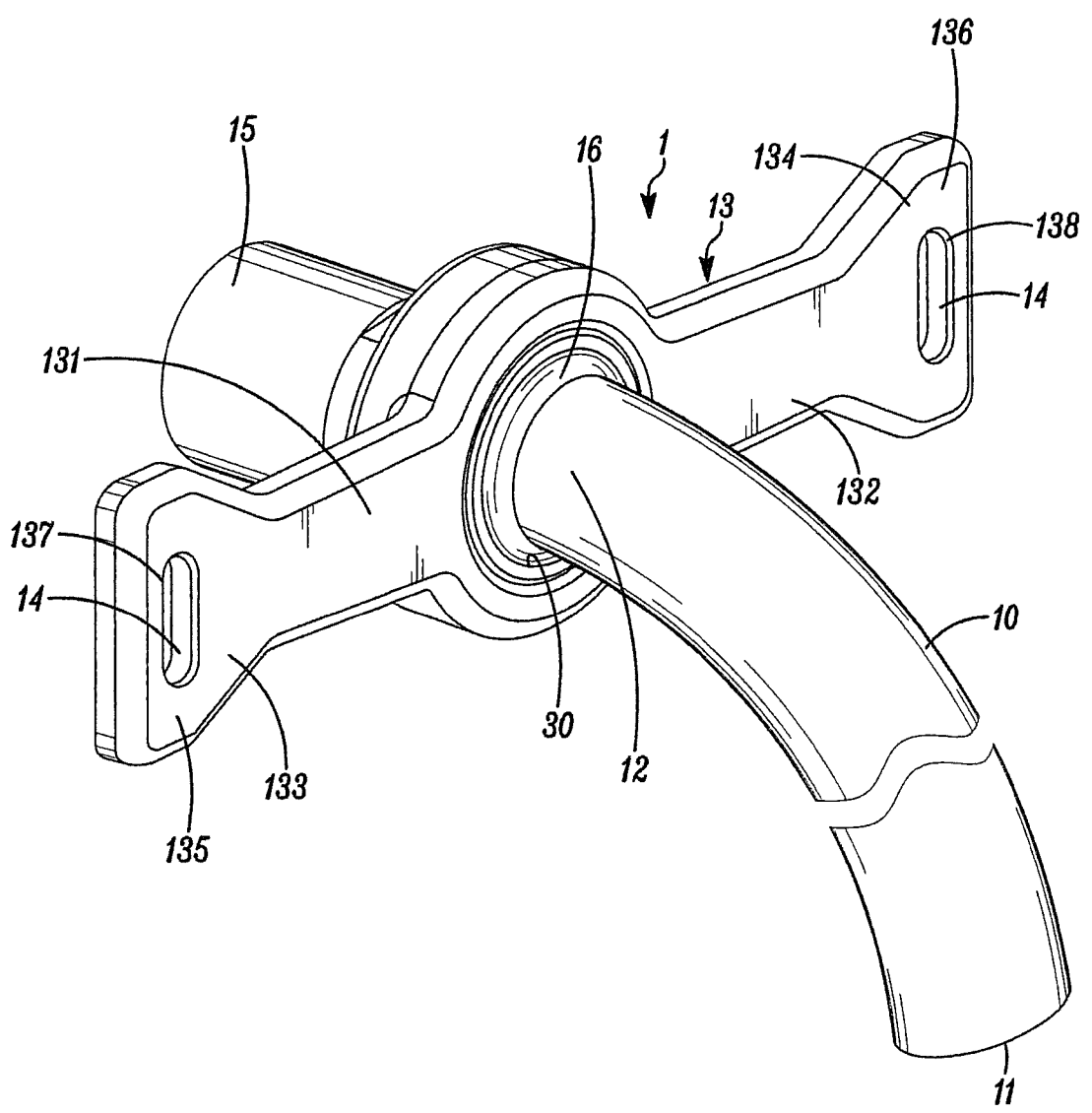
FIG. 1 is a perspective view of the machine end of the tube from its patient side.

With reference first to FIG. 1, the tracheostomy tube 1 has a curved shaft 10 of circular section moulded from a flexible plastics such as silicone. The patient, distal or forward end 11 of the tube 1 is adapted to locate in the trachea. The machine, proximal or rearward end 12 of the tube 1 extends through the tracheostomy and opens externally of the patient. The machine end 12 of the tube supports a laterally extending mounting flange 13 adapted to lie against the skin of the neck and having openings 14 at opposite ends that receive securing means such as the ends of a neck tie (not shown) extending around the neck. Alternatively, the securing means could take the form of sutures threaded through skin adjacent the flange 13. The machine end 12 of the tube 1 also includes an externally tapered 15 mm male connector 15 arranged to receive a cooperating female connector (not shown) at one end of ventilation tubing. The connector 15 illustrated is a separate component from the shaft 10 and is moulded from a harder plastics than that of the shaft. Alternatively, the connector could be an integral component, one piece with the shaft. Where the patient is breathing spontaneously a connector might not be needed so the shaft could be terminated by a low-profile end fitting. The tube 1 is shown without any sealing cuff but it could be provided with such a conventional sealing cuff and other conventional features such as vocalisation fenestrations or suction lumens.

Figure 2:
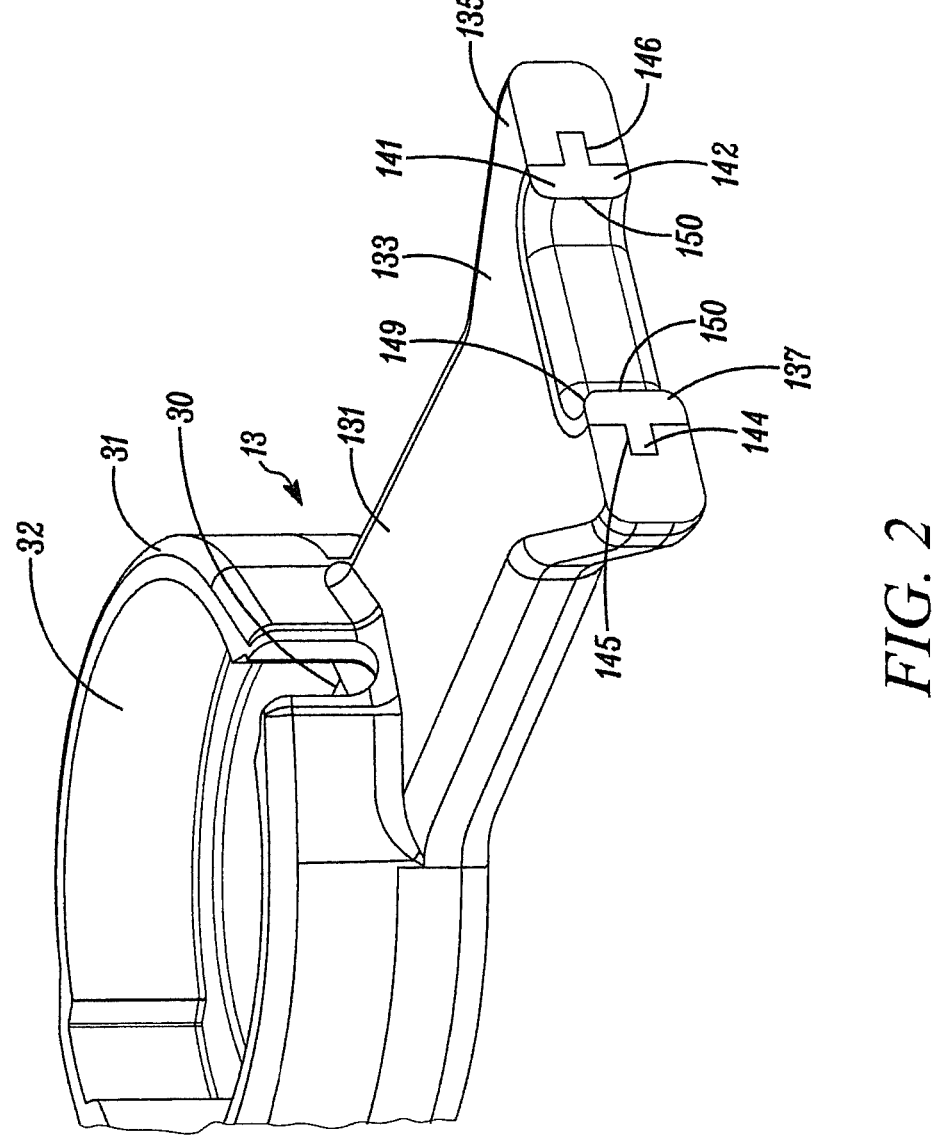
FIG. 2 is an enlarged perspective view of a part of the mounting flange of the tube cut away across one of the flange openings and without the shaft.

With reference now also to FIG. 2, the rear end of the shaft 10 is terminated by an enlarged external circular boss 16 and extends through a central opening 30 in the mounting flange 13. The flange 13 has a circular collar 31 formed around the opening 30 and projecting from the rear face of the flange. The collar 31 forms a circular cavity 32 within which the boss 16 on the shaft 10 is received and to which it is bonded.

Figure 3:
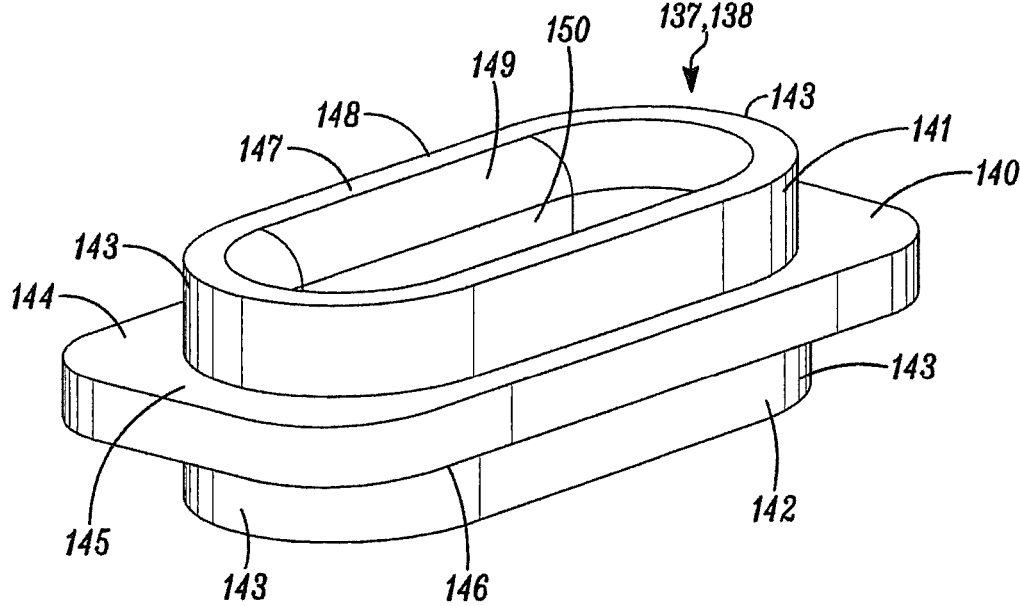
FIG. 3 is an enlarged perspective view of a mounting flange insert.

The mounting flange 13 is moulded from a relatively soft, conformable silicone material, preferably a liquid silicone rubber with a hardness of approximately 70 shore A. This is preferably the same material as forms the shaft 10. The flange 13 has two radial arms 131 and 132 projecting outwardly of the central collar 31 along an axis orthogonal to the plane of curvature of the shaft 10. The inner part of each arm 131 and 132 has a width approximately half the diameter of the collar 31. At its outer end each arm 131 and 132 flares outwardly over a tapered region 133 and 134 to an enlarged region 135 and 136 the width of which is about twice that of the inner part of the arm. The openings 14 for receiving the ends of the neck tie or the like are provided in these enlarged regions 135 and 136 and are reinforced by means of respective inserts 137 and 138 shown more clearly in FIG. 3. The inserts 137 and 138 are retained with the flange 13 by overmoulding the flange material about the outside of the inserts.

The inserts 137 and 138 are also moulded from a silicone material but of a more abrasion-resistant grade of silicone than that forming the main part of the flange 13, namely a heat-cured silicone rubber, such as MED-4070 from Avantor, Inc, having a similar hardness to the material of the flange. It has been found that by making both the inserts and the flange of silicone materials it is possible to achieve a very good bond that is free from cracks and separation even after prolonged use and flexing. The similar hardness of the two materials also has the advantage of ensuring that the inserts do not lead to localised regions of the flange that are stiffer. The inserts 137 and 138 have a generally rectangular shape with a radially extending flat plate 140, which is rectangular with rounded corners and has a thickness about one quarter that of the arms of the flange. From the centre of opposite sides of the plate 140 projects a hollow tubular body formed by identical walls 141 and 142 of a racetrack oval shape with rounded ends 143. The external lateral dimensions of the walls 141 and 142 are less than the external dimensions of the central plate 140 so that the plate forms an annular outer projection, ledge or ring 144 with an upper, rearwardly-facing surface 145 and a lower, forwardly-facing surface 146. The upper and lower surfaces 147 of the walls 141 and 142 have a flat outer region 148 that continues as an inner rounded region 149. This provides a smooth entry to a central, elongate passage 150 through the inserts 137 and 138 forming the openings 14. The inserts 137 and 138 are embedded in the arms 131 and 132 of the mounting flange 13 with the passage 150 through each insert extending at right angles to the length of the arms. The height of the inserts 137 and 138 are equal to the thickness of the arms 131 and 132 so that the opposite surfaces of the arms lie level with the outer flat end regions 148 of the inserts. The ledge 144 of each insert 137 and 138 projects outwardly into the flange material midway across the thickness of the arms 131 and 132. The compatible nature of the silicone materials used in the main part of the flange 13 and in the inserts 137 and 138 means that the flange material forms a secure bond with the outside of the inserts, around the outer surface of the upper and lower walls 141 and 142, along the upper and lower surfaces of the ledge 144 and around its outer edge. The bond between the flange material and the inserts does not require any primer or other pretreatment. The bond formed with the inserts 137 and 138 is resistant bending and flexing of the flange 13 without causing any separation or peeling and without creating fissures or crevices that could allow bacteria to collect. Because the inserts 137 and 138 have a similar hardness to the material of the rest of the flange 13 it avoids any difference in stiffness across the flange. In use, opposite the ends of the neck tie or sutures are threaded through or otherwise secured with the passages 150 in the inserts 137 and 138. The abrasion-resistant nature of the material of the inserts 137 and 138 ensures that force exerted by the neck tie or sutures during use and any rubbing caused by movement does not damage the flange 13, whilst the soft and conformable nature of the flange is not compromised.

The mounting flange 13 is manufactured by first moulding the inserts 137 and 138 from the heat-cured silicone rubber material and subsequently overmoulding the liquid silicone rubber material about the inserts to form the remainder of the flange. To manufacture the complete tracheostomy tube 1, the shaft 10 is moulded separately, preferably from the same silicone material as the flange, or from a similar silicone material that is compatible with the flange material for bonding purposes. The main part of the shaft is overmoulded about or otherwise attached to the patient end of a previously formed connector 15 made of a harder plastics material. The shaft 10 is threaded through the central opening 30 of the flange 13 and a suitable bonding solution is applied to outside of the enlarged boss 16 towards the machine end of the shaft and to the inside 32 of the central collar 31 of the flange.

The invention claimed is:

1. A tracheostomy tube including a shaft and a mounting flange towards a machine end of the shaft, the mounting flange extending radially outwardly of the tube and being provided with an opening towards each end, the opening configured to receive a securing means to retain the tube with a patient's neck, characterised in that the flange is of a first silicone material overmoulded on two reinforcement inserts at respective ones of the openings, and that the reinforcement inserts are of a heat-cured silicone rubber material different from the first silicone material.

2. A tracheostomy tube according to claim 1, characterised in that the silicone material of the flange and of the inserts have a similar hardness.

3. A tracheostomy tube according to claim 1, characterised in that the hardness of both silicone materials is approximately 70 shore A.

4. A tracheostomy tube according to claim 1, characterised in that the first silicone material is a liquid silicone rubber.

5. A tracheostomy tube according to claim 1, characterised in that the inserts include a hollow tubular body with a passage extending therethrough and a projection extending outwardly of the body between opposite ends.

6. A tracheostomy tube according to claim 5, characterised in that the projection is an annular ledge extending around the body.

7. A tracheostomy tube according to claim 5, characterised in that opposite sides of the flange lie level with opposite ends of the body of the inserts, with the passage through each body extending through the thickness of the flange, and with both sides of the projection being covered by material of the flange.

8. A method of manufacture of a mounting flange of a tracheostomy tube including the steps of moulding two inserts of a heat-cured silicone rubber material, both inserts having a passage therethrough and an outer projection, and overmoulding the two inserts about their outer projection with a silicone material different from that of the inserts to form a mounting flange of the tube where the passage through each insert provides an opening towards opposite ends of the flange, the opening configured to receive a securing means.

9. A method according to claim 8, characterised in that the silicone material of the inserts has substantially the same hardness as the silicone material overmoulded about the inserts.

10. A method according to claim 8, characterised in that the tracheostomy tube has a shaft with a patient end and a machine end, and that the method includes attaching the mounting flange with the shaft towards the machine end of the shaft.

11. A tube having a mounting flange manufactured by moulding two inserts of a heat-cured silicone rubber material, both inserts having a passage therethrough and an outer projection, and overmoulding the two inserts about their outer projection with a silicone material different from that of the inserts to form a mounting flange of the tube where the passage through each insert provides an opening towards opposite ends of the flange, the opening configured to receive a securing means.

\* \* \* \* \*